United States Patent [19]

Claude et al.

[11] Patent Number: 4,926,880

[45] Date of Patent: May 22, 1990

[54] METHOD FOR RELIEVING SINUS AND NASAL CONGESTION UTILIZING MICROCURRENTS

[75] Inventors: John P. Claude, Redwood City; Stephen L. Young, San Mateo, both of Calif.

[73] Assignee: Microcurrents, Redwood City, Calif.

[21] Appl. No.: 268,597

[22] Filed: Nov. 8, 1988

[51] Int. Cl.⁵ .............................................. A61N 1/00
[52] U.S. Cl. ................................ 128/800; 128/734; 128/421
[58] Field of Search ............... 128/419 R, 783, 800, 128/801, 419 S, 791, 792, 793, 421, 422, 423, 734

[56] References Cited

U.S. PATENT DOCUMENTS

| | | | |
|---|---|---|---|
| 3,207,151 | 9/1965 | Takagi | 128/419 R |
| 3,866,600 | 2/1975 | Rey | 128/2.1 R |
| 3,894,532 | 7/1975 | Morey | 128/2.1 Z |
| 3,901,214 | 8/1975 | Taaffe | 128/734 |
| 4,112,923 | 9/1978 | Tomecek | 128/1.3 |
| 4,155,351 | 5/1979 | Teshima et al. | 128/734 |
| 4,300,574 | 11/1981 | Briggs | 128/734 |
| 4,408,617 | 10/1983 | Auguste | 128/421 |
| 4,459,995 | 7/1984 | Conners et al. | 128/734 |
| 4,578,635 | 3/1986 | Mee et al. | 128/734 |
| 4,590,942 | 5/1986 | Brenman et al. | 128/419 R |
| 4,630,615 | 12/1986 | Yomtov | 128/734 |
| 4,637,405 | 1/1987 | Brenman et al. | 128/787 |
| 4,697,599 | 10/1987 | Woodley et al. | 128/734 |
| 4,702,259 | 10/1987 | Ferreira et al. | 128/734 |
| 4,763,656 | 8/1988 | Nauman | 128/421 |

*Primary Examiner*—Lee S. Cohen
*Assistant Examiner*—Scott M. Getzow
*Attorney, Agent, or Firm*—Flehr, Hohbach, Test, Albritton & Herbert

[57] ABSTRACT

An apparatus and method for the relieving of sinus congestion by application of microcurrents to the facial areas of a human patient. The apparatus includes a carrying case adapted to be held by one hand of the patient, a power source, an oscillator connected to the power source and a voltage excursion generator. A current limiter limits the net current offset to microcurrent excursions. The apparatus further includes a probe connected to the circuitry for generating microcurrent excursions. The probe has a first electrode adapted to be placed in contact with the facial area of the patient for supplying microcurrents to the patient's sinus area, and a second electrode insulated from the first electrode. The second electrode has a conducting surface adapted to be engaged by the patient's other hand establishing an electrical circuit for microcurrent flowing through the nasal and sinus area. The apparatus further includes a sensor for sensing bodily impedance, and a visual indication that informs and directs the patient to move the probe from facial areas of high tissue impedance to facial areas of low tissue impedance.

17 Claims, 4 Drawing Sheets

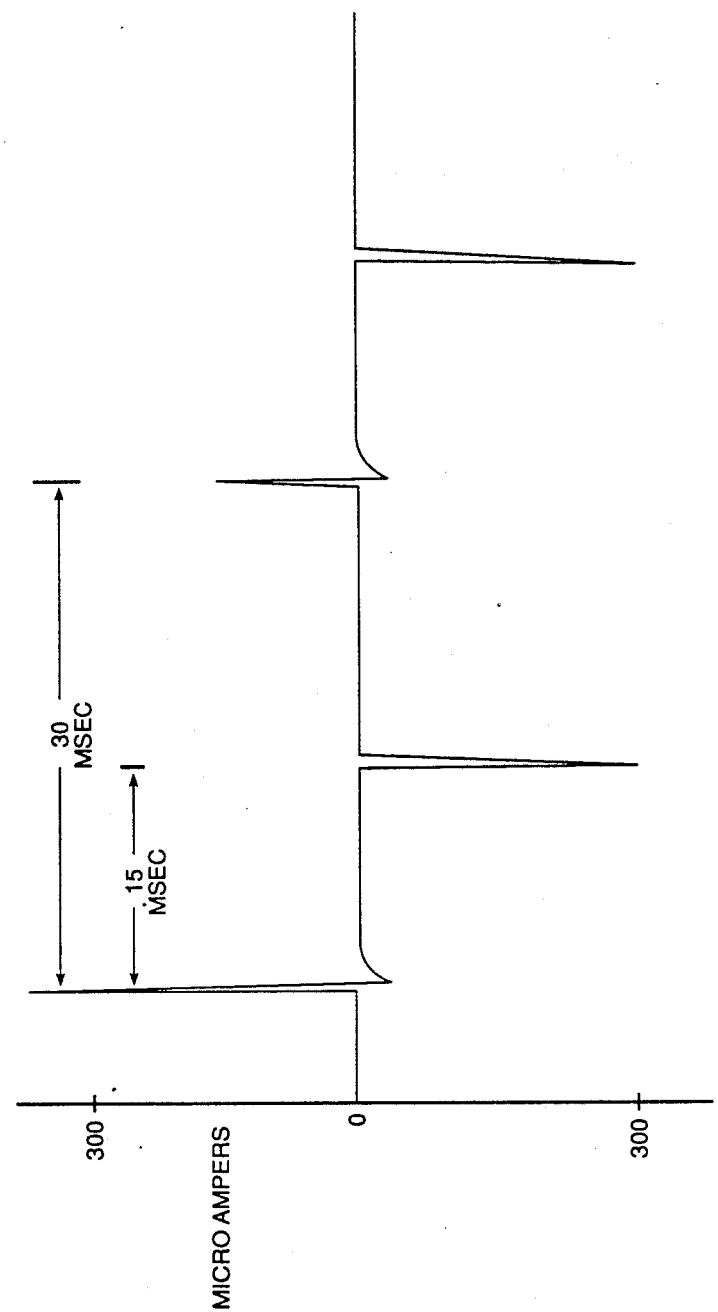

4,926,880

METHOD FOR RELIEVING SINUS AND NASAL CONGESTION UTILIZING MICROCURRENTS

This invention relates to an apparatus and method for relieving sinus and nasal congestion and more particularly to such an apparatus and method which utilizes microcurrents.

Applying therapeutic currents to various parts of the body is known. For instance, the applicant is aware of therapeutic treatment devices which apply currents to the skin, spinal area, muscles of the human body. However, the inventor knows of no such apparatus or method to clear congestion of the nasal and sinus cavity by applying a therapeutic current to the facial area of the patient.

Accordingly, the general object of the present invention is to provide an apparatus and method for relieving sinus congestion utilizing microcurrents.

Another object of the invention is to provide an apparatus and method for relieving sinus congestion by applying current excursions to the sinus area of the patient, with approximately net zero current.

Another object of the invention is to provide an apparatus and method for relieving sinus congestion by applying current excursions or spikes ranging in amplitude of 100 to 300 microamperes at a frequency of 10 hertz to 50 hertz to the sinus area of the patient.

Another object of the present invention to provide an apparatus of the above character which is relatively small, compact and capable of being hand held by the patient.

Another object of the invention is to provide an apparatus of the above character in which the patient utilizes a hand held probe for the purpose of applying a microcurrent to the sinus and nasal area.

Another object of the present invention is to provide an apparatus containing low cost circuitry for the purpose of generating microcurrents.

Another object of the present invention is to provide an apparatus of the above character which has a low power requirement permitting battery operation.

Additional objects and features of the invention will appear from the following description in which the preferred embodiment is set forth in detail in conjunction with the accompanying drawings.

SUMMARY OF THE INVENTION

To achieve the foregoing and other objects of the invention, there is provided an apparatus and method for relieving of sinus and nasal congestion by application of microcurrents to the facial areas of a human patient. The apparatus includes a carrying case adapted to be held by one hand of the patient, and enclosing circuitry having a power source, an oscillator connected to the power source and a voltage excursion generator. A current limiter limits the net current offset to microcurrent excursions. The apparatus preferably includes a probe connected to the circuitry for generating microcurrent excursions. The probe has a first electrode adapted to be placed in contact with the facial area of the patient for supplying microcurrents to the patient's sinus area, and a second electrode insulated from the first electrode. The second electrode has a conducting surface adapted to be engaged by the patient's other hand establishing an electrical circuit for microcurrent flowing through the nasal and sinus area. The apparatus preferably also includes a sensor for sensing bodily impedance, and an indicator responsive to the sensor to inform and direct the patient to move the probe from facial areas of high tissue impedance to facial areas of low tissue impedance.

BRIEF DESCRIPTION OF THE DRAWINGS

FIG. 6 is a graph showing the therapeutic current excursions generated by the circuitry of FIG. 5 and applied to the sinus are of the patient.

DESCRIPTION OF THE PREFERRED EMBODIMENT

Figure 1:
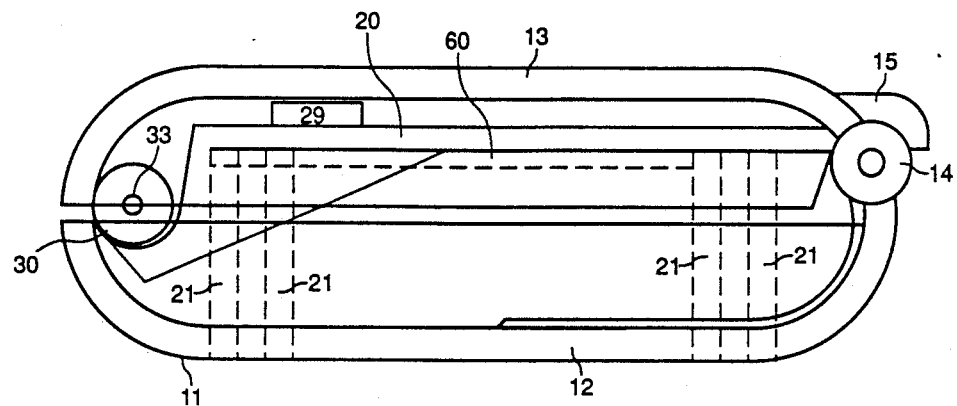
FIG. 1 is a side view of the apparatus incorporating the present invention and particularly showing the portable case in a closed position.

The present invention includes a hand held case containing circuitry for generating microcurrent excursions which relieve sinus and nasal congestion. The current is applied to the patient's facial areas by a first electrode mounted in a probe electrically connected to the circuitry. A second electrode, located around the circumference of the probe, contacts the patient's hand when using the probe. During operation, a complete circuit is made as current flows from the first electrode, through the patient's facial area and body, to the second electrode engaged by the patient's hand holding the probe.

Current should be applied to low impedance areas of the face. A sensor in the device senses bodily impedance, and generates a visual and audio indicators informing and directing the patient to move the probe from facial areas of high tissue impedance to facial areas of low tissue impedance.

The preferred embodiment is shown in FIGS. 1-5. Apparatus 10 consists of a protective molded plastic portable hand-held carrying case 11 comprising a clam shell shaped bottom section 12 with four upwardly extending walls. A clam shell shaped top section 13, with four downwardly extending walls, is pivotally mounted to bottom section 12 at hinge mechanism 14. The top section 13 is movable between an open position and a closed position with respect to the bottom section 12. A protruding stop 15 on the top section 13 near hinge member 14, prevents top section 13 from opening beyond a substantially vertical position with respect to bottom section 12. During operation, carrying case 11 is held in one hand of the patient with top 13 in the open position. A mirror 16, recessed in the inner portion of top section 13, enables the user-patient to observe the facial area while top section 13 is in an open position.

A liner 20 supports the user display and control interface of apparatus 10. Liner 20 is mounted over the circumference of the open portion of bottom section 12. Four support posts 21 emerge upward from the four corners of bottom section 12. Posts 21 are made of a plastic material and provide structural support for liner 20. A PC board 60, containing the circuitry shown in FIG. 5 for generating microcurrents, is structurally embedded between liner 20 and structural support posts 21. The entire assembly, including liner 20 mounted over the circumference of the open portion of bottom section 12 and support posts 21 are ultrasonically welded together, forming a sealed enclosure with PC board 60 firmly embedded in between.

Figure 5:
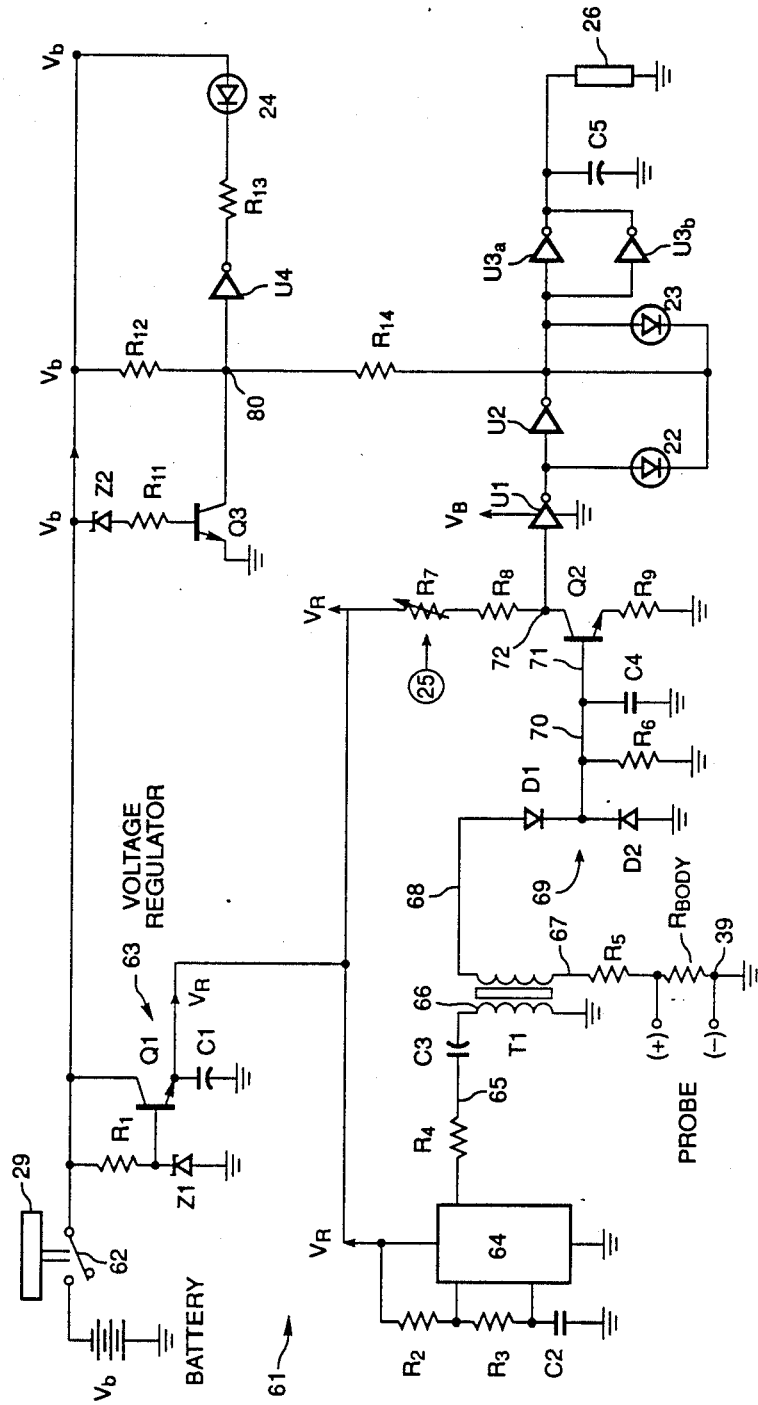
FIG. 5 is a circuit diagram of the circuitry utilized in the apparatus shown in FIGS. 1-4 for generating therapeutic microcurrent excursions.

The liner 20 holds a green LED low tissue impedance indicator 22, a red LED high tissue impedance indicator 23, a low battery indicator yellow LED 24, a user sensitivity slide control 25, an audio annunciator 26, probe storage compartment 27 and compression grooves 28a and 28b for securing probe 30 in storage compartment 27. An ON/OFF button 29, electro-mechanically connected to an electrical switch 62 shown in FIG. 5 is also present on liner 20. Operation of circuit 61 and switch 62 is discussed below.

Figure 4:
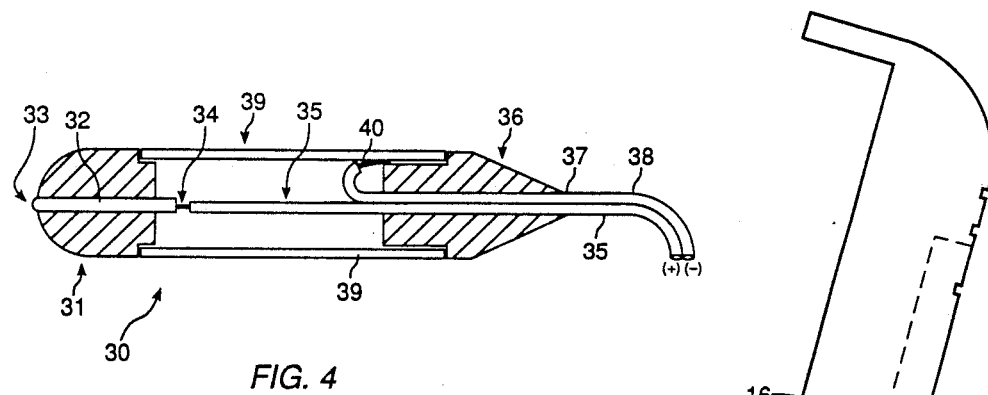
FIG. 4 is a cross sectional view of the probe in the apparatus of FIGS. 1 and 2.

As best shown in FIG. 4, probe 30 is an elongated member of generally cylindrical form. Extremity 31, located at one end of the probe 30, is substantially hemispherical in shape, and is comprised substantially of a non-conductive material. A first electrode 32 is centrally disposed in the distal extremity 31 and includes a rounded exterior tip 33 adapted to be applied to the facial area of the patient. A first electrical contact 34 provides an electrical connection with a first conductor 35. Conductor 35, connected to the microcurrent generator located on circuit 61 supplies a microcurrent to tip 33 via contact 34 and first electrode 32.

A second distal extremity 36, located at the other end of the probe 30, is essentially comprised of a non-conductive material, and is adapted to centrally dispose a second conductor 37. Conductors 35 and 37 are electrically insulated from one another and together comprise an electrical cord 38 connecting probe 30 to the microcurrent generating circuit 61 shown in FIG. 5.

A second electrode 39, insulated from the first electrode 32, has an electrically conductive surface adapted to be engaged by the patient's other hand when the probe is being used. The second electrode 39 is in the form of a band of conducting material which forms a part of the exterior cylindrical surface of the probe. At contact point 40, the second electrode 39 is electrically connected to the second 37 which in turn is connected to an electrical ground point in circuit 61.

During operation of the apparatus 10, the electrode tip 33 is placed in contact with the sinus and nasal area of the patient's face. Microcurrent excursions, illustrated in FIG. 6, generated by circuit 61, follow the electric path defined by conductor 35, contact point 34, electrode 32 and electrode tip 33 into the facial area of the patient. The preferred embodiment of the microcurrent excursion range from 100 to 300 microamperes. In general, the current would be limited to a range no greater than 0 to 500 microamperes. Once inside the body, the current will flow through the sinus tissue and facial area, down the neck, to the arm and hand holding probe 30. The electric circuit is completed as current passes from the hand holding probe 30 to the second electrode 39, through second conductor 37 and finally to a ground point located at circuit 61. The desired microampere current excursions are applied to the nasal area of the patient in this manner.

In the most effective use of apparatus 10, the microcurrent should be applied to areas of low tissue impedance. Tissue impedance can vary from area to area of the patient based on several factors; including skin temperature, tissue thickness, and bodily secretions such as perspiration and oil. The present invention provides indicators, including; a green low tissue impedance indicator 22, a red high tissue impedance indicator 23 and an audio annunciator 26. These indicators inform and direct the patient to move the probe from areas of high impedance to low impedance as bodily conditions affecting impedance change.

When probe 30 is in contact with a low impedance area of the face, the green visual LED 22 will remain lit indicating to the patient to leave the probe in that location. Furthermore, a confirming audio annunciator 26 will simultaneously provide a beeping or buzzing sound indicating again that the user should keep the probe stationary in that low impedance location. Alternatively, as bodily conditions change and the tissue impedance increases in the area where probe tip 33 is in contact with the skin, the present invention is designed to inform the patient by de-energizing the low tissue impedance indicator 22 and audio annunciator 26 and energizing the red LED 23 to indicate high impedance.

Figure 2:
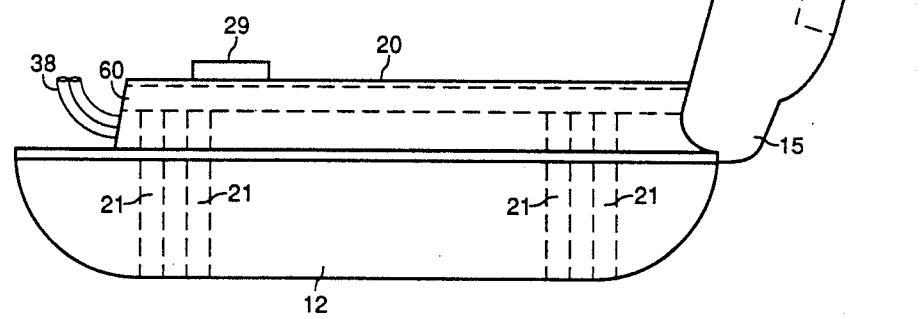
FIG. 2 is the same side view of the apparatus shown in FIG. 1 and particularly showing the portable case in an opened position.
Figure 3:
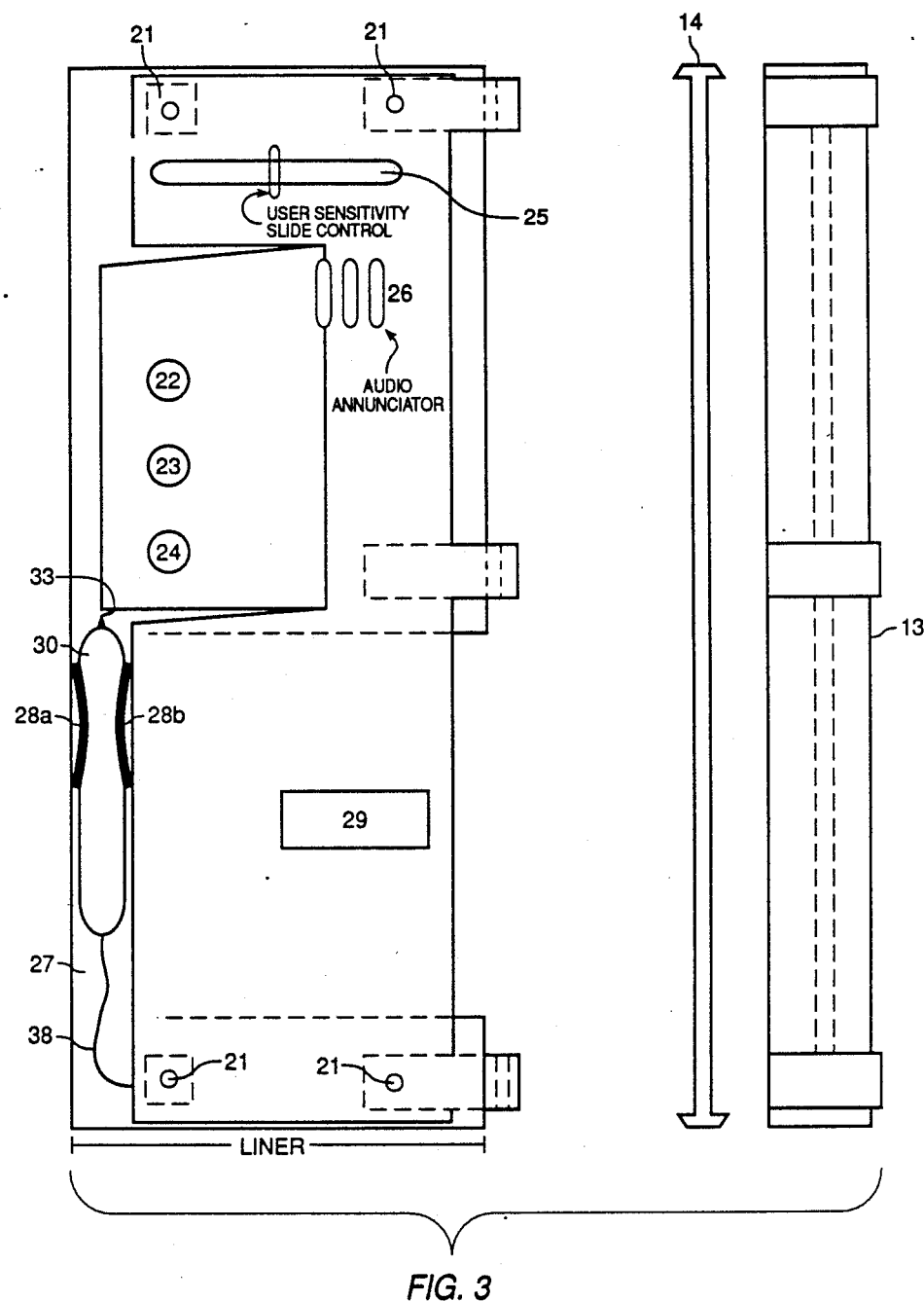
FIG. 3 is top plane view of the apparatus of FIGS. 1 and 2.

The circuitry 61 of FIG. 5 for accomplishing the aforementioned features is herein described. The energizing of circuit 61 is accomplished by the opening and closing of case 11. In FIG. 1, top section 13 is in a closed position resting on bottom section 12. In this position, top section 13 rests on ON/OFF button 29 forcing it into its OFF position. Alternatively, as shown in FIG. 2, top section 13 is shown in an open position and button 29 is in its ON position. As best illustrated in FIG. 5, ON/OFF button 29 is electro-mechanically connected to close electric switch 62, which electrically connects circuit 61 with battery voltage $V_b$ when button 29 is in the ON position.

Voltage regulator 63 is energized by battery voltage $V_b$ when switch 62 is in the closed position. Voltage regulator's 63 output is a steady voltage $V_r$ generated by transistor Q1. Resistor R1, connected between $V_b$ and the base of Q1, acts as a voltage to current convertor for providing a base current to Q1. Zenor diode $Z_1$, connected between the base of Q1 and ground, provides a voltage regulator keeping the base voltage essentially constant. Capacitor C1, connected between Q1's collector and ground removes any voltage signal noise thereby producing a constant output voltage $V_r$.

An oscillator 64, manufactured by Texas Instruments, is electrically connected to receive voltage $V_r$ and generate in response thereto a series of positive square wave pulses with a frequency ranging from 10–50 Hertz and an amplitude of $V_r$. The timing characteristics of oscillator 64 are determined by resistors R2, R3 and C2 connected to oscillator 64 in accordance to the chip manufacturer's specifications.

A wave shaping RC differentiator 65, comprising in series capacitor $C_3$ and resistor $R_4$, is electrically connected to receive the square wave output from oscillator 64 and to generate in response thereto a series of positive and negative square wave pulses of an amplitude approximately $\frac{1}{2} V_r$. A transformer T1 is electrically connected to receive differentiator's 65 output at transformer T1's primary coil 66. Transformer's T1 primary coil 66 steps up or amplifies the alternating current component of the square wave pulses into a series of positive and negative voltage excursions or spikes above and below 0 volts and with a net direct current offset. A first end 6 of the secondary coil of transformer T1 is serially connected to R5, which acts as a current limiting device limiting the therapeutic current excursions through the patient's body to the desired range of 100 to 300 microamperes as illustrated in FIG. 6. Patient body impedance is designated $R_{body}$ on FIG. 5. The therapeutic microcurrent excursions are conducted to probe tip 33 via cord 38 and first conductor 35. According to the invention, it is essential that the therapeutic wave form have the following characteristics. First, it must maintain its excursion or spike form. Current excursions or spikes tend to have a penetrating and probing effect in the skin and bodily tissue of the patient, and hence, facilitate current conductivity through bodily tissue. A second characteristic of the microcurrent excursions of the present invention is that the area under the positive current excursions equals the area under the negative current excursions. The net current of the waveform must approximate zero. A net current with either a positive or a negative value may burn the patient.

The current excursions of 100 to 300 microamperes interact with the electrical properties of the sinus and nasal tissue cells of the patient. It is believed that cell receptor ions and nerve function in control of the nasal and sinus mucosa are favorably influenced by current stimulation.

The remaining portion of the circuitry diagram on FIG. 5 is devoted to the operation of user control, display and the sensitivity control features located on liner 20. A voltage doubler 69, comprising of oppositely opposed diode pair $D_1$ and $D_2$, is serially connected to a second output end 68 of the secondary coil of transformer T1. Diodes $D_1$ and $D_2$ filter out and allow to pass to ground the negative voltages excursions while doubling the amplitude of the positive voltage excursions. An integrator 70, comprising resistor $R_6$ and a capacitor $C_4$, are each electrically connected between the diode pair output $D_1$ and $D_2$ and ground. Integrator 70 sums the amplitude of the positive voltage excursions into a variable direct voltage level output, and consequently a varying direct current output. The integrator 70 output varies according to Ohms Law ($V=IR$). As bodily impedance increases, the voltage and current output of the integrator 70 decreases. Conversely, as body impedance decreases, the integrator voltage and current output of integrator 70 increases.

Transistor Q2, electrically connected to integrator's 70 output, receives the variable voltage level waveform which establishes a current (hereinafter $I_b$) at transistor base 71. The sensitivity of Q2 is altered in response to changes of base current $I_b$ which in turn varies in response to skin impedance. Voltage source $V_r$ is connected to transistor Q2's collector 72. User sensitivity slide control 25 is electrically connected to variable potentiometer R7 and resistor R8, which together, provide a means for the user to selectively control the collector current present at transistor Q2 collector 72. User selectivity slide control 25 in effect permits the user to selectively change the gain of Q2. As gain of Q2 is increased, the sensitivity is increased to detect changes in skin impedance. Sensitivity control is required because of the tendency of skin impedance to change as the perspiration and oil content of the patient's skin varies.

If $I_b$ is less than the forward bias threshold required to turn on Q2, it indicates the probe 30 is being applied to an area of high tissue impedance. Q2 will remain in a non-switching state and pull up resistors R7 and R8 will provide a high input signal to invertor U1's input which is electrically connected to collector 72. Under these circumstances, U1's output will be low providing a de-energizing signal to low tissue impedance indicating green LED 22. A second invertor U2 is electrically connected to invert U1's low output into a high, thereby energizing low tissue impedance indicating red LED 23. A third invertor pair U3a and U3b, electrically connected to U2 output drives the audio annunciator 26 in compliance with green LED 22. Capacitor C5, connected between invertors U3a and U3b and audio annunciator 26 removes unwanted voltage noise variations from the invertor pair U3a and U3b output.

If the $I_b$ has increased due to a decrease of tissue impedance, or the patient selectively increased Q2 sensitivity by adjusting the resistance of R7 with user control 25, or a combination thereof, Q2 will switch into conducting mode. The collector current at collector 72 will flow through Q2's emitter 73 to ground. R9 connected between the emitter 73 and ground acts as a pull-down resistor directing collector current to ground. Under these circumstances, U1 will receive a low input, thereby generating a high output and energizing green low tissue impedance indicator 22. Invertor U2 will invert the U1 high output to a low, de-energizing red LED 23. U3a and U3b will invert U2 low output to a high which will energize audio annunciator 26 in compliance with low tissue impedance indicator 22.

The remaining portions of circuitry 61 is dedicated to operate low battery indicator 24. A zenor diode $Z_2$ is electrically connected to receive battery voltage $V_b$ at its input. Zenor diode's $Z_2$ switching threshold voltage is set to correspond with the minimum voltage required to properly drive circuitry 61.

Zenor diode $Z_2$ output and resistor $R_{11}$ are electrically connected to the base of transistor Q3 A resistor $R_{12}$ is electrically connected between $V_b$ and the collector of Q3. The collector of Q3 is also electrically connected to the input of invertor U4. Low battery indicator yellow LED 24 is serially connected to resistor $R_{13}$ and invertor U4 output.

When $V_b$ is greater than Zenor diode $Z_2$ threshold, $Z_2$ switches on and $R_{11}$ provides a base current to Q3 turning Q3 into a switching mode. With Q3 on, the current created by $V_b$ and $R_{12}$ travels through the emitter of Q3 to ground, providing a low input to U4. The inverted high output of U4 acts to de-energize low batter indicator LED 24 through resistor $R_{13}$.

Conversely, when $V_b$ falls below the zenor diode $Z_2$ threshold voltage, $Z_2$ will provide no current to Q3 base and Q3 will remain in a non-switching mode. The current created by $V_b$ and $R_{12}$ will provide a high input to invertor U4. The invertor low output of U4 acts to energize low battery indicator yellow LED 24.

A resistor $R_{14}$ is serially connected between $R_{12}$ and the green LED 22 and red LED 23. When $V_b$ is greater than the zenor diode $Z_2$ threshold voltage, as noted above, the current created by $V_b$ and $R_{14}$ travels through the emitter of Q3. As a result, node 80 will be held low and green LED 22 and red LED 23 remain operable as described above. Conversely, when $V_b$ is less than $Z_2$ threshold voltage, node 80 will be at a high voltage and LEDs 22 and 23 are disabled. Consequently, when yellow LED 24 is energized, green LED 22 and red LED 23 will be rendered inoperable, indicating to the patient to change the battery source.

While the present invention has been described with reference to a specific embodiment, the description is merely illustrative of the invention and is not to be construed as limiting the invention. Various modifications may occur to those skilled in the art without departing from the true spirit and scope of the invention as defined by the appended claims.

What is claimed is:

1. A method for relieving sinus and nasal congestion, the method comprising the steps of:
   generating periodically repeating microcurrent excursions;
   applying said microcurrent excursions to a patient's face adjacent the patient'nasal area; and
   generating a perceptible signal when said microcurrent excursions are being applied to a low impedance region of said patient's face;
   whereby, when said microcurrent excursions are applied to low impedance regions of a patient's face adjacent the nasal area, said microcurrent excursions relieve the patient's sinus and nasal congestion.

2. The method of claim 1, wherein said first generating step includes the step of generating alternating positive and negative microcurrent excursions having a frequency in the range of 10 to 50 hertz and having a net current of approximately zero amperes, each said microcurrent excursion having an amplitude in the range of 0 to 500 microamperes.

3. The method of claim 1, wherein said first generating step includes the step of generating alternating positive and negative microcurrent excursions having a frequency in the range of 10 to 50 hertz and having a net current of approximately zero amperes, each said microcurrent excursion having an amplitude in the range of 100 to 300 microamperes.

4. The method of claim 1, wherein said step of generating a perceptible signal further comprises the steps of:
   measuring the impedance encountered by said microcurrent excursions, comparing said measured impedance to a predetermined threshold impedance value, and generating a perceptible signal when said measured impedance is less than said predetermined threshold impedance value.

5. The method of claim 4, wherein said perceptible signal comprises an audible signal.

6. The method of claim 5, wherein said step of generating a perceptible signal further includes generating a visible signal of a predetermined color.

7. The method of claim 4, wherein said step of generating a perceptible signal further includes the step of generating a second, distinct perceptible signal when said measured impedance is more than said predetermined threshold impedance value;
   whereby said patient is formed by said second distinct perceptible signal that said microcurrents should be applied to a different region of said patient's face.

8. The method of claim 4, wherein said predetermined threshold value is selectively adjusted to compensate for variations of skin impedance measurements.

9. A method for relieving sinus and nasal congestion, the method comprising the steps of:
   providing a hand held probe having first and second electrodes, said second electrode being positioned to be in contact with the patient's hand while holding said probe;
   generating periodically repeating microcurrent excursions;
   supplying said microcurrent excursions to said first electrode of said hand held probe;
   contacting said first electrode of said hand held probe to said patient's face adjacent the nasal region;
   applying said microcurrent excursion to a patient'face adjacent the patient's nasal area; and
   generating a perceptible signal when said microcurrent excursions are being applied to a low impedance region of said patient's face;
   whereby said microcurrent excursions propagate through the patient's nasal area, body and bend holding said probe to said second electrode to complete an electrical circuit, and when said microcurrent excursions are applied to low impedance regions of a patient's face adjacent the nasal area, said microcurrent excursions relieve the patient's sinus and nasal congestion.

10. The method of claim 9, wherein said applying step further comprises the steps of:
    moving said probe over the region of the patient's face adjacent the nasal area until said perceptible signal is generated.

11. The method of claim 9, wherein said step of generating a perceptible signal further comprises the steps of:
    measuring the impedance encountered by said microcurrent excursions, comparing said measured impedance to a predetermined threshold impedance value, and generating a perceptible signal when said measured impedance is less than said predetermined threshold impedance value.

12. The method of claim 11, wherein said perceptible signal comprises an audible signal.

13. The method of claim 11, wherein said step of generating a perceptible signal further includes generating a visible signal of a predetermined color.

14. The method of claim 11, wherein said step of generating a perceptible signal further includes the step of generating a second, distinct perceptible signal when said measured impedance is more than said predetermined threshold impedance value;
    whereby said patient is informed by said second distinct perceptible signal that said microcurrents should be applied to a different region of said patient's face.

15. The method of claim 11, wherein said predetermined threshold value is selectively adjusted to compensate for variations of skin impedance measurements.

16. A method for relieving sinus and nasal congestion, the method comprising the steps of:
    generating periodically repeating microcurrent excursions; and
    applying said microcurrent excursions to low impedance regions of a patient's face adjacent the patient's nasal area;
    whereby, when said microcurrent excursions are applied to low impedance regions of a patient's face adjacent the nasal area, said microcurrent excursions relieve the patient's sinus and nasal congestion.

17. The method of claim 16, wherein said generating step includes the step of generating alternating positive and negative microcurrent excursions having a frequency in the range of 10 to 50 hertz and having a net current of approximately zero amperes, each said microcurrent excursion having an amplitude in the range of 100 to 300 microamperes.

* * * * *